(12) United States Patent
Gründeman

(10) Patent No.: US 8,764,646 B2
(45) Date of Patent: Jul. 1, 2014

(54) SURGICAL EXPANSION DEVICE

(75) Inventor: Paul Frederik Gründeman, Amsterdam (NL)

(73) Assignee: UMC Utrecht Holding B.V., Utrecht (NE)

( * ) Notice: Subject to any disclaimer, the term of this patent is extended or adjusted under 35 U.S.C. 154(b) by 1319 days.

(21) Appl. No.: 10/834,128

(22) Filed: Apr. 29, 2004

(65) Prior Publication Data
US 2005/0245960 A1   Nov. 3, 2005

(51) Int. Cl.
*A61B 1/32* (2006.01)

(52) U.S. Cl.
USPC ............................ 600/207; 606/191; 606/192

(58) Field of Classification Search
USPC .................................. 606/191–192; 600/207
See application file for complete search history.

(56) References Cited

U.S. PATENT DOCUMENTS

| | | | | |
|---|---|---|---|---|
| 3,774,596 A | * | 11/1973 | Cook | 600/184 |
| 5,308,327 A | * | 5/1994 | Heaven et al. | 604/103.09 |
| 5,309,896 A | * | 5/1994 | Moll et al. | 600/207 |
| 5,575,759 A | * | 11/1996 | Moll et al. | 600/207 |

* cited by examiner

*Primary Examiner* — Darwin Erezo
*Assistant Examiner* — Diane Yabut
(74) *Attorney, Agent, or Firm* — Young & Thompson

(57) ABSTRACT

A surgical device for application in a treatment performed on the human or animal body with the aim of providing access to a surgical site in the body by exerting a force, upon expansion of the device at the location of the surgical site, on the organs and/or tissues at the surgical site, e.g. for mobilizing and/or supporting organs and/or tissues, the surgical device including an expansion structure, at least one fluid reservoir, and a conduit for conveying fluid from the reservoir to the expansion structure.

9 Claims, 1 Drawing Sheet

SURGICAL EXPANSION DEVICE

BACKGROUND OF THE INVENTION

The invention is related to a surgical device for application in a treatment performed on the human or animal body with the aim of providing access to a surgical site in said body, comprising expansion means suitable for exerting a force on the organs and/or tissues at said surgical site, e.g. for mobilising and/or supporting said organs and/or tissues, upon expansion of said device at the location of the surgical site, at least one fluid reservoir as well as means for conveying fluid from said reservoir to the expansion means with the aim of expanding said expansion means.

Such a surgical device is disclosed in U.S. Pat. No. 5,218,586. It consists of an expandable tip mounted at the end of a manipulation tube. The tip can be brought into a puncture type opening in e.g. the abdominal, pelvic or chest cavities. In particular, said prior art device is suitable for application in laparoscopic or thorascopic procedures. The expandable tip itself consists of a generally hollow inflatable device member similar to a balloon. It is fabricated from a non-toxic, relatively strong, flexible and resilient material such as polypropylene or a similar type of impervious material which is flaccid and deformable in the unexpanded state. The internal space of said balloon type member can be inflated by either introducing a liquid or a gas therein.

Said prior art surgical device has several disadvantages. Due to the elastic character of the balloon type member, an energy build up occurs during expanding the balloon. The wall thereof is stretched during the process of filling the balloon, and in the case of filling the balloon with a gas energy build-up also occurs due to compression of the gas. In case in that state an inadvertent rupture of the balloon occurs, said energies are suddenly released. This results in a disastrous shock effect, which may cause severe trauma to the organs or tissues in the vicinity.

A further disadvantage of the prior art surgical device is related to the balloon shape thereof. Although a somewhat better access to the surgical site can be obtained thereby upon expansion, it nevertheless also has a shielding effect with respect to the directly adjoining tissues or organs. In those cases, the expansion member has to be moved out of the way, which complicates the surgical operation.

SUMMARY OF THE INVENTION

The object of the invention is to provide a surgical device of the type described before which does not pose the risk of causing trauma, even in the case of an inadvertent failure of the expansion means. A further object is to provide a surgical device which allows a better access to the surgical site in question. This object is achieved in that the expansion means comprises a sheet type material having a relatively low bending stiffness and a relatively high in-plane stiffness.

The expansion means according to the invention can be stowed into a small package, as a result of the bendable character of the material thereof. Upon expansion however, it will not stretch as a result of the high in-plane stiffness thereof. Thus, the expansion means itself will not store energy itself, as it does not, or hardly not, stretch. In case an inadvertent rupture occurs, no stored energy is therefore freed. The rupture can occur in an orderly fashion, without causing trauma to the surrounding tissues or organs. In this connection, preferably, a liquid is used as expansion medium. As is known a liquid is hardly compressible, in any case in comparison to a gas. Thus, upon expanding the device according to the invention, hardly any energy will be stored in the expansion liquid either. In case of a rupture of the expansion means, the liquid will spill over at the surgical site, but the release of liquid will not occur with a large impulse thereby mitigating the effects of the spill-over.

Preferably, the expansion means comprises at least one elongate expansion member which has a longitudinal shape in the expanded state. Such elongate expansion member offers the possibility to form a cavity at the surgical site which has an improved accessibility. In this connection, more preferably the expansion means has at least two elongate expansion members which are angled with respect to each other's longitudinal direction in the expanded state. In case the expansion means comprises at least one tension member the length of which is smaller than the sum of the lengths of the elongate expansion members, the expanded device will obtain a predetermined, desired shape which is prescribed by the dimensions of the various members. It will be clear that the expansion members will then delimit a specific open area, which allows a better accessibility of the enclosed area.

Furthermore, according to a specific embodiment, at least three elongate expansion members can be provided which together constitute a triangle. The frame thus obtained may further be used to form expansion means having specific height, length and width dimensions. As a result, the multiple elongate expansion members thus applied may constitute a spatial structure. As an example, a tetrahedron is given, but other structures such as a cube and the like are possible as well. All these structures have in common that they offer a frame after expansion of the several expansion members, which to that end preferably have interconnected fluid chambers allowing a simultaneous expansion. The frames thus obtained are able to create a free space within the body at the surgical site. The surgeon is thus able to reach through the open sides of the expanded frame, and is therefore able to perform intricate operations at the site without being hampered by the expansion means itself.

Preferably, the surgical device comprises at least one restrictor for restricting the expansion of the expansion means. By means of such restrictor, the expansion means in question can be urged into a specific, prescribed shape, for instance a curved shape. In the latter case, the restrictor comprises a tension member, in particular a pull member.

BRIEF DESCRIPTION OF THE SEVERAL VIEWS OF THE DRAWINGS

The invention will now be described further with reference to an embodiment of the surgical device as shown in the figures.

DETAILED DESCRIPTION OF THE PREFERRED EMBODIMENTS

Figure 1:
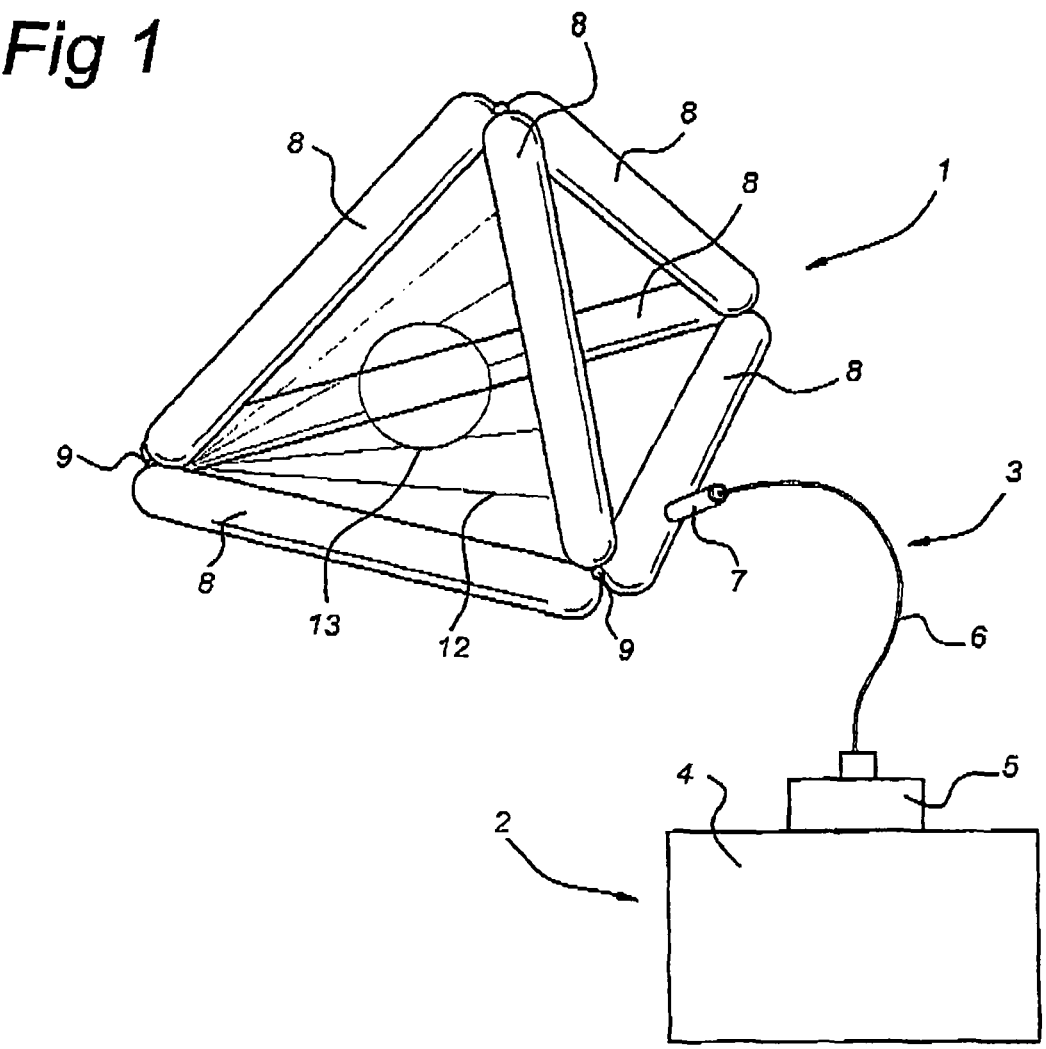
FIG. 1 shows a surgical device according to the invention.

FIG. 1 shows a surgical device according to the invention, comprising the expansion means 1 which is in FIG. 1 is shown in the expanded state. Furthermore, there is at least one fluid reservoir as well as a means 3 for conveying fluid from said reservoir 2 to the expansion means.

The fluid reservoir comprises a container 4 which holds an amount of preferably liquid fluid, which by means of pump 5 is pumped into the line 6. The line 6 in turn is connected to a connection port 7, which gives access to the internal space of the expansion means 1.

Said expansion means comprises six elongate members 8, which together constitute a tetrahedron. The elongate expansion members 8 are connected to each other at the nodes 9. Also, the expansion members contain a fluid chamber 10, which fluid chambers 10 at the location of the nodes 9 are interconnected.

In a rest state, the elongate members 10 are deflated, which means that they can be reduced to relatively small dimensions for introduction at a surgical site. After positioning the deflated expansion means 1, liquid is fed to the internal space, in particular the fluid chambers 10 thereof, thus inflating the expansion means 1 to the shape of the tetrahedron as shown in FIG. 1.

The advantage of such form of the expanded expansion means 1 is clear: first of all a hollow space is formed within the tetrahedron, giving the surgeon access to sites which are otherwise difficult to reach. The open phases between the elongate members 8 enable the surgeon to reach through the apparatus, enabling him a further improved access to the surgical site.

Additionally, a flexible web 12 is mounted between three of the expansion members. Said flexible web 12 is stretched upon expansion of said members 8, whereby the formation of an open surgical site is further enhanced. A fenestration hole 13 is provided in said flexible web 12 so as to enable the surgeon to reach the surgical target site. Further webs 12 may be mounted to the other expansion member 8 as well.

Figure 2:
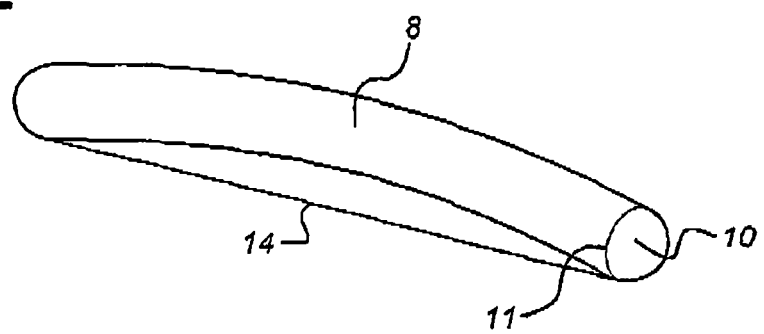
FIG. 2 shows a component of the surgical device according to FIG. 1.

FIG. 2 shows a possible embodiment of a tension member 8 provided with a pull member 14. The pull member 14, e.g. wire, is connected to the opposite ends of the tension member 8. The length of the pull member 14 is somewhat smaller than the length of the tension member 8 between the mutual connection points. Thereby, upon expansion of the tension member 8, it is brought into a slightly curved shape due to the fact that it is restricted in its full expansion by the restrictor 14. In this way, the surgical device according to the invention can be brought into a specific, desired shape upon expansion thereof.

The invention claimed is:

1. A surgical device for application in a treatment performed on the human or animal body to provide access to a surgical site in said body, the device comprising:
   expansion means (1) for exerting a force on the organs or tissues at said surgical site;
   a fluid reservoir (2); and
   means (3) for conveying fluid from said reservoir (2) to expand said expansion means (1) through a connection port (7), the connection port providing access to the internal space of the expansion means (1), wherein,
   said expansion means (1) has elongated expansion members (8), the expansion members being angled with respect to each other's longitudinal direction in an expanded state, and said expansion members each having opposite ends which are spaced apart in their longitudinal direction,
   a flexible web (12) extends between at least two of the expansion members (8), the at least two expansion members (8) bordering an open side of the expansion means, the open side i) being void of a web or other closure and ii) configured to provide unrestricted access from an inside of the expansion means to an outside of the expansion means,
   a pull member (14) is connected to the opposite ends of at least one of the expansion members (8), a length of said pull member between said opposite ends being less than a length of said at least one of the expansion members (8) between said opposite ends so that said at least one of the expansion members (8), when in the expanded state, is urged by said pull member (14) to have a slightly curved shape by restricting a full expansion of said at least one expansion member (8), and
   the expansion means (1), during and after expansion thereof, forms a frame with the open side.

2. A method for providing access to a surgical site in a human or animal body, comprising the steps of:
   providing an inflatable surgical device, comprising
      an expansion means (1),
      at least one fluid reservoir (2),
      means (3) for conveying fluid from said reservoir (2) to expand said expansion means (1) through a connection port (7) to give access to the internal space of the expansion means (1),
      wherein the expansion means has elongate expansion members (8) angled with respect to longitudinal directions of the expansion members in an expanded state, and the expansion members (8), in the expanded state, form a frame with open sides and each having opposite ends which are spaced apart in said longitudinal directions, the open sides being void of a web or other closure and configured to provide unrestricted access from an inside of the expansion means to an outside of the expansion means, and
      wherein a flexible web (12) extends between at least two of the elongate expansion members (8);
   placing the surgical device at the surgical site near an organ or tissue in the human or animal body;
   providing the surgical device with at least one restrictor (14) for restricting an expansion of the expansion means, said restrictor being connected to the opposite ends of at least one of the expansion members (8), a length of said restrictor between said opposite ends being less than a length of said at least one of the expansion members (8) between said opposite ends;
   inflating the elongate expansion members (8) so the elongate expansion members (8) form the frame and the surgical device exerts a force against the organ or tissue to establish a free space within the human or animal body, the open sides being open during said inflating of the expansion members (8);
   obtaining a specific predetermined shape of the expansion means upon the inflating of the expansion means with said at least one restrictor (14), said at least one restrictor (14) restricting a full expansion of said expansion means;
   performing operations at the surgical site through the open sides of the frame.

3. The method according to claim 2, wherein the at least one restrictor (14) is provided as a wire connected to opposite ends of one of the elongate members (8) of the expansion means (8).

4. A surgical device for application in a treatment performed on the human or animal body to provide access to a surgical site in said body, the device comprising:
   a plurality of elongate expansion members (8), each expansion member, when expanded in an expanded mode, having a longitudinal shape and angled with respect to each other's longitudinal direction, and said expansion members each having opposite ends which are spaced apart in a longitudinal direction, an end of each of said expansion members attached to an end of another of said expansion members;
   a fluid reservoir (2);
   means (3) for conveying fluid from said reservoir (2) to expand said expansion members (8) through a connection port (7), the connection port providing access to an internal space of the expansion members (8); and a pull member (14), having a total length between opposite ends that is less than a total length between the opposite ends of at least one of the expansion members (8), the pull member (14) connected to the opposite ends of the at least one of the expansion members (8) so that, when in the expanded mode, the at least one of the expansion members (8) is urged by said pull member (14) to have a slightly curved shape by restricting a full expansion of said at least one expansion member (8), wherein, in the expanded mode, said expansion members (8) form a frame of a spatial structure, the spatial structure having a height, a width, a length, and open sides between the expansion members, the open sides being void of a web or other closure, and wherein said sides are open during expansion of said expansion members (8) into the expanded mode.

5. The surgical device according to claim 4, the device further comprising:

a flexible web (12) with a fenestration hole (13), the flexible web (12) mounted between at least two of said expansion members (8), the fenestration hole (13) configured to enable a surgeon to reach a surgical target site.

6. The surgical device according to claim 4, the device, wherein, said plurality has three of said expansion members (8), and said three expansion members, in the expanded mode, form a triangle having an opening between said expansion members.

7. The surgical device according to claim 4, wherein said plurality has six of said expansion members (8), each end of any one of said expansion members joined to respective ends of two others of said expansion members, said expansion members (8), in the expanded mode, forming a tetrahedron having open sides between said expansion members.

8. The surgical device according to claim 4, wherein each end of any one of said expansion members is joined to respective ends of two others of said expansion members, said expansion members (8), in the expanded mode, forming a cube.

9. The surgical device according to claim 4, wherein each of the expansion members comprises a sheet type material enclosing an internal chamber to receive an expansion medium, the sheet type material forming, upon expansion by injection of the expansion medium into the chamber, a longitudinal shape with an elongated, tubular outer surface.

* * * * *